US008413521B2

(12) United States Patent
Myers (10) Patent No.: US 8,413,521 B2
(45) Date of Patent: Apr. 9, 2013

(54) APPARATUS AND METHOD FOR OVER-PEAK LOADING FOR CREEP-RUPTURE TESTING

(75) Inventor: Jeffrey Lynn Myers, Madison Township, OH (US)

(73) Assignee: General Electric Company, Schenectady, NY (US)

( * ) Notice: Subject to any disclaimer, the term of this patent is extended or adjusted under 35 U.S.C. 154(b) by 251 days.

(21) Appl. No.: 13/053,631

(22) Filed: Mar. 22, 2011

(65) Prior Publication Data

US 2012/0240688 A1    Sep. 27, 2012

(51) Int. Cl.
*G01N 3/08*    (2006.01)

(52) U.S. Cl.
USPC .............................................. 73/826; 73/808

(58) Field of Classification Search ............. 73/760, 73/808, 826
See application file for complete search history.

(56) References Cited

U.S. PATENT DOCUMENTS

| | | | | |
|---|---|---|---|---|
| 3,622,795 A | * | 11/1971 | Dorman et al. | 356/40 |
| 4,006,624 A | * | 2/1977 | Annino et al. | 73/23.23 |
| 4,149,407 A | * | 4/1979 | Strom et al. | 73/794 |
| 4,248,096 A | * | 2/1981 | Marcum | 73/828 |
| 4,599,219 A | * | 7/1986 | Cooper et al. | 422/430 |
| 4,746,858 A | | 5/1988 | Metala et al. | |
| 5,262,730 A | * | 11/1993 | Smith et al. | 324/650 |
| 5,345,826 A | | 9/1994 | Strong | |
| 6,938,494 B2 | | 9/2005 | Takada et al. | |
| 7,353,715 B2 | * | 4/2008 | Myers | 73/837 |
| 7,584,670 B2 | | 9/2009 | Myers | |
| 7,779,747 B2 | | 8/2010 | Myers | |
| 2009/0314100 A1 | | 12/2009 | Myers | |

OTHER PUBLICATIONS

Instron, "Stress-Rupture Testing System / Model C", www.instron.com, 2 pages, Nov. 2010.
Instron, "Model M3 / Creep and Stress Rupture Tester", www.instron.com, Copyright Instron 2003, 2 pages, Nov. 2010.

* cited by examiner

*Primary Examiner* — Max Noori
(74) *Attorney, Agent, or Firm* — General Electric Company; Sushupta T. Sudarshan; David J. Clement (57) ABSTRACT

A method and testing apparatus including first and second load adjusting mechanisms for cyclically applying and reducing first and second tensile loads on a specimen and first and second controllers connected to the first and second load adjusting mechanisms for independently cycling the loads which are additive. Cycling the first and second loads for peak loading and over-peak loading the specimen respectively and controlling first and second loading rates and first and second dwell periods of first and second cycles for peak loading and over-peak loading respectively. The second load adjusting mechanism may include an inflatable over-peak device resting on a plate mounted to a frame of the apparatus. The device includes a hollow housing for supporting the second load, an inflatable bladder within the housing, and a bladder lower portion extending out of an opening at a bottom of the housing when the bladder is inflated.

28 Claims, 6 Drawing Sheets

APPARATUS AND METHOD FOR OVER-PEAK LOADING FOR CREEP-RUPTURE TESTING

BACKGROUND OF THE INVENTION

1. Field of the Invention

The present invention relates to apparatus and method for tensile testing of specimens under applied and reduced loads and, more particularly, to apparatus and method for over-peak loading for creep-rupture testing.

2. Description of Related Art

Evaluating the condition and determining the future performance of mechanical components, such as gas turbine engine components, that operate in a high stress regime of materials is important to industry for maximizing the life of the components and limitations of remaining useful life, or life expended. Components which operate at high temperatures, such as greater than about 900. degree. F. (482. degree. C.), where a combination of creep and thermal aging of the components' material is of prime concern and require special consideration in order to achieve an acceptable remaining useful life estimation.

Many systems and methods for testing and estimating the useful life of such components involve applied mechanical loads that are cyclic and vary over a time period. Of particular interest is low cycle fatigue (LCF) testing, and especially sustained-peak LCF (SPLCF) testing, to examine the fatigue crack growth behavior over time of materials used to make gas turbine engine components. The fatigue crack growth behavior of specimens comprising these materials is characterized by applying cyclic loads using a "creep-rupture" frame. Various cyclic tensile amplitudes are applied, and the number of cycles required to pull apart the specimen under those conditions is recorded. Stress and/or fatigue damage is evidenced by a decrease in strength and stiffness. In some cases, the tests can be terminated after some number of cyclic loadings and then breaking the specimen (i.e., a tensile test) to determine the residual strength. The data from such destructive tests are usually characterized by empirical means and generalized by implication or extrapolation to a variety of service conditions for which the materials were not specifically tested in the laboratory.

Evaluation of test specimens for long hold-time fatigue and crack growth, as well as other stress-related properties, may be accomplished using a creep-rupture frame or lever arm tester such as the one disclosed in U.S. Pat. No. 5,345,826 (Strong), issued Sep. 13, 1994, which schematically illustrates a typical "creep-rupture" frame/lever arm tester. This device consists of a lever arm of from typically twelve to twenty inches in length that is pivotally mounted on a vertical frame at a point along the lever arm's length between its center and an end to which one end of a test specimen is attached. The other end of the test specimen is attached to a fixed base plate. When weights are applied or loaded on the opposite end of the lever arm, a tensile force is exerted on the test specimen according to the formula $t=(wl)/d$, where t is the tensile force exerted on the test specimen, w is the weight applied to the far end of the lever arm, l is the distance between the lever arm pivot point and the end carrying the applied weights, and d is the distance between the lever arm pivot point and the end connected to the test specimen. Tensile testing of the specimen is initiated by applying the force t.

Creep-rupture frames/lever arm testers can be equipped to cyclically apply and reduce the load (e.g., created by the weights) on the test specimen. The cyclical application and reduction of the load in creep-rupture frames/lever arm testers is conventionally carried out by using either a standard pneumatic cylinder or a scissor jack lift.

An apparatus and method for cyclical application and reduction of loads in tensile testing of specimens that provides a relatively smooth application and reduction of the applied loads is disclosed in U.S. Pat. No. 7,353,715 by Jeffrey Lynn Myers (the present inventor), issued Apr. 8, 2008, and assigned to the same assignee as the present patent application, the General Electric Company. U.S. Pat. No. 7,353,715 is incorporated herein by reference.

Another type of closely related tensile testing of specimens under applied and reduced loads is over-peak fatigue testing. The loading is typically performed on relatively expensive servo-hydraulic testing machines that are a great deal more expensive as is the testing as compared to creep-rupture testing machines and systems.

There exists a need for apparatus and methods for over-peak fatigue testing that are less expensive than those currently employed. There exists a need for apparatus and methods for over-peak fatigue testing that provides control of both over-peak load magnitude and dwell time. It is also desirable to provide a testing machine that evaluates creep-rupture and over-peak loading.

SUMMARY OF THE INVENTION

A test specimen tensile testing apparatus includes first and second load adjusting mechanisms for cyclically applying and reducing first and second tensile loads on the test specimen and first and second controllers controllingly connected to the first and second load adjusting mechanisms and operable for independently cycling the first and second loads respectively on the test specimen.

The first and second loads are additive in one embodiment of the apparatus and the first and second controllers are operable for cycling the first and second loads for peak loading and over-peak loading the test specimen respectively. The first and second controllers are operable for controlling first and second loading rates and first and second dwell periods of first and second cycles of loading on the test specimen respectively.

One embodiment of the second load adjusting mechanism includes an inflatable over-peak device that rests or is supported on a support plate mounted to a frame of the tensile testing apparatus. One embodiment of the inflatable over-peak device includes a hollow housing with a flat top for supporting the second load, an inflatable bladder disposed within the housing, and a bladder lower portion which extends out of an opening at a bottom of the housing when the bladder is inflated.

An exemplary embodiment of the tensile testing apparatus includes a load train section connected to the test specimen, a pivotable lever arm extending generally horizontally and pivotable on a frame of the tensile testing apparatus, first and second load adjusting mechanisms for cyclically applying and reducing first and second tensile loads on the test specimen and first and second controllers controllingly connected to the first and second load adjusting mechanisms and operable for independently cycling the first and second loads respectively on the test specimen. The first and second load adjusting mechanisms extend generally vertically downwardly from a load adjusting end of the lever arm, the load train section extends generally vertically downwardly from a load train end of the lever arm.

The first load adjusting mechanism may include a fluidic mechanical muscle that contracts and extends in length for cyclically applying and reducing the first load.

A method for over-peak load testing the test specimen includes mounting the test specimen in the load train section of the tensile testing apparatus, cyclically applying and reducing tensile first and second loads with the first and second load adjusting mechanisms respectively on the test specimen, and independently cycling the first and second loads using first and second controllers controllingly connected to the first and second load adjusting mechanisms respectively.

One embodiment of the method further includes using a fluidic mechanical muscle that contracts and extends in length as the first load adjusting mechanism and the cyclically applying and reducing the first load includes contracting and extending the fluidic mechanical muscle in length respectively. The embodiment of the method further includes using an inflatable over-peak device as the second load adjusting mechanism. The over-peak device rests or is supported on a support plate mounted to a frame of the tensile testing apparatus. The inflatable over-peak device includes a hollow housing supporting the second load, an inflatable bladder disposed within the housing, and a bladder lower portion which extends out of an opening at a bottom of the housing when the bladder is inflated. The cyclically applying and reducing of the second load includes deflating and inflating the bladder respectively.

The method may further include applying the first and second loads together for over-peak loading of the specimen and removing the second load while holding the first load constant for peak loading and controlling first and second loading rates and first and second dwell periods of first and second cycles during the cycling of the first and second loads respectively wherein the second cycle is substantially shorter than the first cycle. The first and second loading rates may be the same.

BRIEF DESCRIPTION OF THE DRAWINGS

The foregoing aspects and other features of the invention are explained in the following description, taken in connection with the accompanying drawings where.

DETAILED DESCRIPTION OF THE INVENTION

As used herein, the term "load" refers to any mass, weight, force, etc., to which a test specimen is subjected to by a system, apparatus and/or method of this invention.

As used herein, the term "applying the load" refers to subjecting the test specimen to a load, including increasing the amount or degree of load that the specimen is subjected to.

As used herein, the term "reducing the load" refers to partially or completely decreasing, diminishing, eliminating, etc., the load the test specimen is subjected to.

As used herein, the term "cyclically applying and reducing a load" refers to at least one cycle where the load is applied and reduced, in any order thereof, i.e., apply and reduce load, reduce and apply load, etc. Typically, the cycle involves first applying the load progressively or sequentially, and subsequently reducing the load progressively or sequentially. The cyclic application and reduction of the load can be a single cycle, or more typically is a plurality of such cycles (i.e., for at least two cycles). The load can be applied and reduced in the same manner or pattern each cycle or can be applied and reduced in a different manner or pattern each cycle. The load can also be applied and held (i.e., sustained) at a specified level (i.e., the load is neither increasing nor decreasing) for the same or different discrete period of time one or more times during the cycle, can be increased and/or can be decreased progressively or sequentially at the same or different rates, or any combination thereof, during each cycle.

As used herein, the term "closed loop system" refers to a control system having a feedback mechanism (e.g., a mechanical and/or electronic signal or plurality of signals) for adjusting, altering, controlling, etc., the application and/or reduction of the load on the test specimen. The feedback mechanism used in a closed loop system typically provides a substantially linear and proportional application and/or reduction of the load on the test specimen.

As used herein, the term "open loop system" refers to a control system that does not utilize a feedback mechanism.

As used herein, the terms "creep-rupture frame" and "lever arm tester" refer interchangeably to a device that typically comprises a lever arm of mechanical advantage typically from about twelve to about twenty inches (from about 30.5 to about 51 cm.) in length that is pivotally supported on a fixed vertical member of a frame at a point along the lever arm's length between its center and an end to which one end of a test specimen is attached, with the other end of the test specimen typically being attached to a base plate or platform (e.g., of a cross-frame), and where one or more weights are applied or loaded on the opposite end of the lever arm. See FIG. 1 and the corresponding description in U.S. Pat. No. 5,345,826 (Strong), issued Sep. 13, 1994 (herein incorporated by reference), which schematically illustrates a typical "creep-rupture" frame/lever arm tester. Suitable creep-rupture frame/lever arm testers for use herein include those made by SATEC, ATS, etc.

As used herein, the term "fluidic mechanical muscle" refers to a device which typically contracts in length in a relatively controlled manner upon being pressurized with a fluid (i.e., a gas such as air or a liquid such as ethylene glycol) and extends in length in a relatively controlled manner upon the release of the pressurized fluid. Contraction of the fluidic mechanical muscle typically causes the application of the load to the test specimen, while the extension of the fluidic mechanical muscle typically causes the reduction of the load. The fluidic mechanical muscle has characteristics such that when it is pressurized, the relative length of the muscle typically contracts substantially linearly with the applied pressure while at the same time creating substantial forces suitable for actuating, lifting, moving, positioning, etc, the load, and conversely extends substantially linearly with the reduction (release) of pressure.

Because of their different construction, and especially their inherent non-dynamic, relatively controlled contraction and extension in length, the fluidic mechanical muscles useful herein differ from standard dynamic pneumatic cylinders. Fluidic mechanical muscles suitable for use herein can be of the "McKibben" type of fluid contractile actuator or "muscle" that typically includes a cylindrical sheath formed from a flexible mesh (sometimes referred to as a "braiding" structure) comprising a plurality of interconnected rhomboidal or rhombus shaped segments that are secured to connectors at each end of the sheath with a bladder comprising a strong expandable material disposed within the sheath, and with an inflation line connected to the bladder through which a pressurizing fluid may be introduced for the purpose of inflating or expanding the bladder within the cylindrical sheath, along with appropriate valves on the inflation line to direct fluid from a pressurizing source into the bladder for inflation (contraction), as well as to allow fluid to escape from the bladder for release/deflation (extension). See, for example, U.S. Pat. No. 4,739,692 (Wassam et al.), issued Apr. 26, 1988 (herein incorporated by reference), which describes the operation of a "McKibben" type of fluid contractile actuator or "muscle". In operation, the "McKibben" type fluidic contractility actuator or "muscle" is connected between two fixed points using a connector with the bladder deflated. The cylindrical sheath formed from the flexible mesh is connected between two flexible points and ideally experiences a very slight tensile stress in order to ensure that the sheath when connected in its extended or "relaxed" position between the two points is at a minimum diameter. The inflation line is connected to the source of pressurizing fluid that may be compressible, i.e., a gas, or incompressible, i.e., a liquid. The fluid when introduced into the bladder expands it against the enclosing mesh sheath, causing it to expand diametrically and contract longitudinally generating an extremely large contractile force between the connectors. See also U.S. Pat. No. 4,615,260 (Takagi et al.), issued Oct. 7, 1986; U.S. Pat. No. 5,158,005 (Negishi et al.), issued Oct. 27, 1992; U.S. Pat. No. 5,165,323 (Sato), issued Nov. 24, 1992; and U.S. Pat. No. 5,201,262 (Negishi et al.), issued Apr. 13, 1993 (herein incorporated by reference), as well as U.S. Pat. No. 4,841,845 (Beullens), issued Jun. 27, 1989; U.S. Pat. No. 6,067,892 (Erickson), issued May 30, 2000; and U.S. Pat. No. 6,223,648 (Erickson), issued May 21, 2001 (herein incorporated by reference), for other fluidic mechanical muscles of the "McKibben" type of fluid contractile actuator or "muscle" that are potentially suitable for use herein. Examples of commercially available fluidic mechanical muscles suitable for use herein include those made by Festo Corporation of the "Fluidic Muscle MAS" series, including Model No. MAS-10-N--AA-MCFK, Part 187594; Model No. MAS-10-N--AA-MOFK, Part 187595; Model No. MAS-40-N-459-AA-MCIK, Part 187605; Model No. MAS-40-N--AA-MCIK, Part 187606); Model No. MAS-40-N--AA-MOKK, Part 187607; Model No. MAS-20-N--AA-MCHK, Part 187617; Model No. MAS-20-N--AA-MCGK, Part 187618; Model No. MAS-20-N--AA-MOHK, Part 187619; Model No. MAS-10-, Part 534201; Model No. MAS-20-, Part 534202; and Model No. MAS-40-, Part 534203, etc.

As used herein, the term "test specimen" refers to any specimen, including a component, part, etc., comprising a material of interest, or a specimen fabricated, manufactured, etc., from a material of interest that is subjected to a load by the system, apparatus and/or method disclosed herein. The test specimen can be of any suitable shape or configuration, including rectangular, cylindrical, etc. Typically, the test specimen has a reduced gauge or width at the middle section thereof (e.g., is "dog-bone shaped") to force elongation of the material at the middle of the specimen when subjected to the load.

As used herein, the terms "tension testing" and "tensile testing" refer interchangeably to a test format where the test specimen is subjected to a substantially longitudinal stretching, pulling, etc. force when the load is applied thereto. Representative, but non-limiting examples of tension or tensile testing include low cycle fatigue testing, sustained-peak low cycle fatigue testing, creep-rupture testing, high strain rate peak testing, bend testing, crack growth testing, etc.

As used herein, the terms "low cycle fatigue testing" or "LCF testing" refer interchangeably to a slower or lower loading cycle speed fatigue type test where the cycle is usually about 30 Hertz or less, and is typically in the range of from about 0.3 to about 1 Hertz.

As used herein, the terms "sustained-peak low cycle fatigue testing" or "SPLCF testing" refer interchangeably to a type of LCF test where the peak load applied to the test specimen is held or sustained at a specified level for a discrete period of time.

As used herein, the term "bend testing" refers to a test format where the test specimen is supported at its respective ends and the load is applied proximate to the midpoint thereof between the respective ends.

As used herein, the terms "mission cycle testing" or "simulation testing" refer interchangeably to testing that is intended to represent an actual operation (i.e., real life phenomena) and is typically carried out using a closed loop test system. Mission cycle/simulation testing typically refers to a type of field testing (e.g., of an engine) where the engine is operated, data is taken and brought back to a mission or simulator operation lab (either manually or more typically electronically), and the data is then used to program (typically using a computer), for example, a simulated, but real life stress cycle on the test specimen of interest.

As used herein, the term "creep-rupture test" refers to a test format where a static and consistent load is applied to the test specimen and where the elongation of the test specimen during the application of the load is measured.

As used herein, the term "fracture toughness" refers to the measurement of the resistance of a specimen being tested to extension of a crack. See Davis, ASM Materials Engineering Dictionary (1992), p. 72.

As used herein, the term "fatigue crack growth test" refers to a test format that measures of the rate of growth of a crack in a test specimen over time or over an applied load cycle(s).

Figure 1:
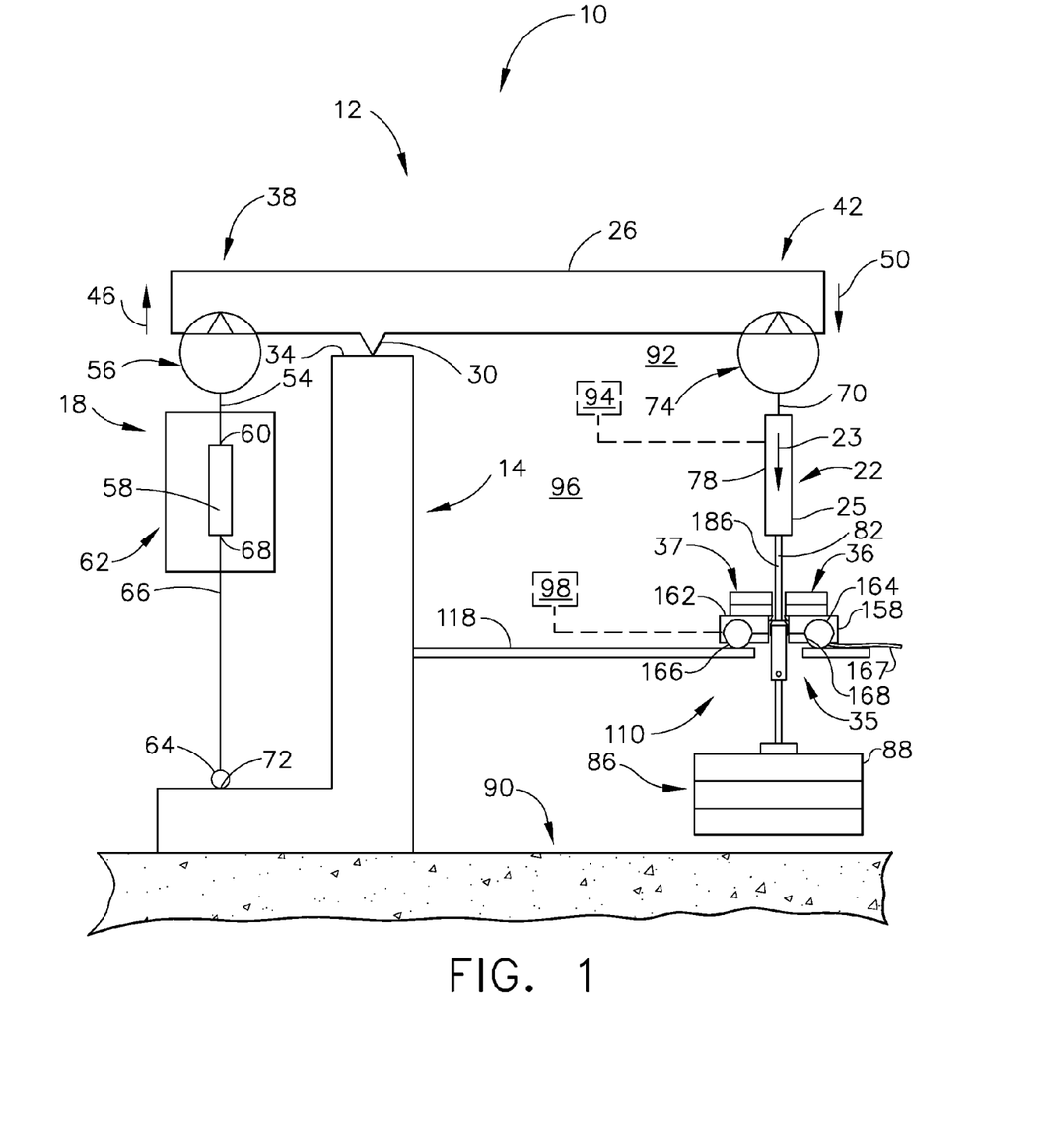
FIG. 1 is a schematic view illustration of an apparatus for over-peak loading and rupture testing.

Referring now to the drawings, illustrated in FIG. 1 is a tensile testing system 10 that uses a tensile testing apparatus in the form of a lever arm tester 12. The tester 12 includes a generally L-shaped frame 14, a generally vertically extending first load train section 18 associated with the frame 14, and a generally vertically extending first load adjusting section 22 associated with the frame 14. A first load adjusting mechanism 25 is used for applying and reducing a first tensile load 23 from the first load adjusting section 22 to the first load train section 18. The first load is applied (in the form of tensile stress) or reduced on a test specimen 58. The mechanism 25 is illustrated herein as including a pivoting generally horizontally extending lever arm 26. The mechanism 25 includes a fulcrum or pivot point 30 for balancing the lever arm 26 on a top end 34 of the longer length vertical segment of frame 14 about which the lever arm 26 swings or pivots. The lever arm 26 also has a load train end 38 and a load adjusting end 42.

Referring to FIG. 1, as a load adjusting end 42 of the lever arm 26 moves generally downwardly (indicated by a downward pointing arrow 50) about a horizontally axis defined by the pivot point 30, the load train end 38 moves generally upwardly (indicated by an upward pointing arrow 46), and vice versa when the load adjusting end 42 moves generally upwardly about the horizontal axis defined by the pivot point 30. The particular position of the pivot point 30 along the length of the lever arm 26 between ends 38, 42 can be moved horizontally to adjust the multiple of load effectively transferred by arm 26 from the first load adjusting section 22 to the first load train section 18.

The effect is defined by the formula $t=(wl)/d$, where t is the tensile force exerted on the test specimen 58, w is the weight or load applied to the load adjusting end 42 of the lever arm 26, l is a distance between pivot point 30 and load adjusting end 42, and d is the distance between pivot point 30 and the load train end 38. The load train end 38 is connected or attached to the test specimen 58 such that the applied force, t imparts a stress to the test specimen. The closer pivot point 30 is to load train end 38, and conversely away from load adjusting end 42 (i.e., d is smaller and l is larger), the greater the multiple of load that is effectively transferred or applied from the first load adjusting section 22 to the first load train section 18, i.e., the greater the value for t. For example, a load (w) of 10 units in load adjusting section 22 can be translated by arm 26 into a force (t) of 200 units applied to the first load train section 18 (and test specimen 58) if the ratio of l:d is 20:1.

Referring to FIG. 1, the first load train section 18 includes an upper pull rod 54 that is adjacent to and connected or attached, at its upper end, to the load train end 38 of arm 26 by joint 56. The upper pull rod 54 is also adjacent to and connected or attached, at its lower end 60, to the test specimen 58. The load train section 18 can also include an environmental chamber such as a furnace indicated generally as 62 which encloses the specimen 58. The first load train section 18 further includes a lower pull rod 66 that is adjacent to and is connected or attached, at its upper end 68, to the specimen 58, and that is also adjacent to and is connected or attached, at its lower end 72, to the frame 14. The lower pull rod 66 is illustrated as being connected to the frame 14 by a universal joint 64. The lower pull rod 66 remains essentially stationery by being attached to frame 14 and, thus, when the upper pull rod 54 is moved vertically upwardly when the load train end 38 of arm 26 pivots upwardly in the direction indicated by arrow 46, the test specimen 58 is subjected to a tensile force.

The first load adjusting section 22 includes an upper connector 70 that is adjacent to and is connected or attached, at its upper end, to the load adjusting end 42 of arm 26 by joint 74. The first load adjusting section 22 includes a fluidic mechanical muscle 78 that is adjacent to and is connected or attached, at its upper end, to the lower end of connector 70. As the muscle 78 contracts in length, the load in first load adjusting section 22 is applied (via arm 26) to the first load train section 18, and conversely, as muscle 78 extends in length, the load in the first load adjusting section 22 is reduced (via arm 26) on the first load train section 18. A first cyclic loading system 92 includes a first controller 94 to cycle the loading on the test specimen 58 by controlling extension and contraction of the muscle 78.

The first load adjusting section 22 further includes a lower connector 82 connected or attached, at its upper end, to the lower end of muscle 78, and is also connected or attached, at its lower end, to a first load 86 typically made up of first weights 88. The first load 86 is illustrated as being spaced above the ground or main surface 90, thus, indicating that system 10 is at a point in the testing cycle where muscle 78 is in a contracted state and where the first load 86 is thus being applied (via arm 26 and load train section 18) to specimen 58. The tensile testing system 10 is illustrated herein is an "open loop" system.

Figure 2:
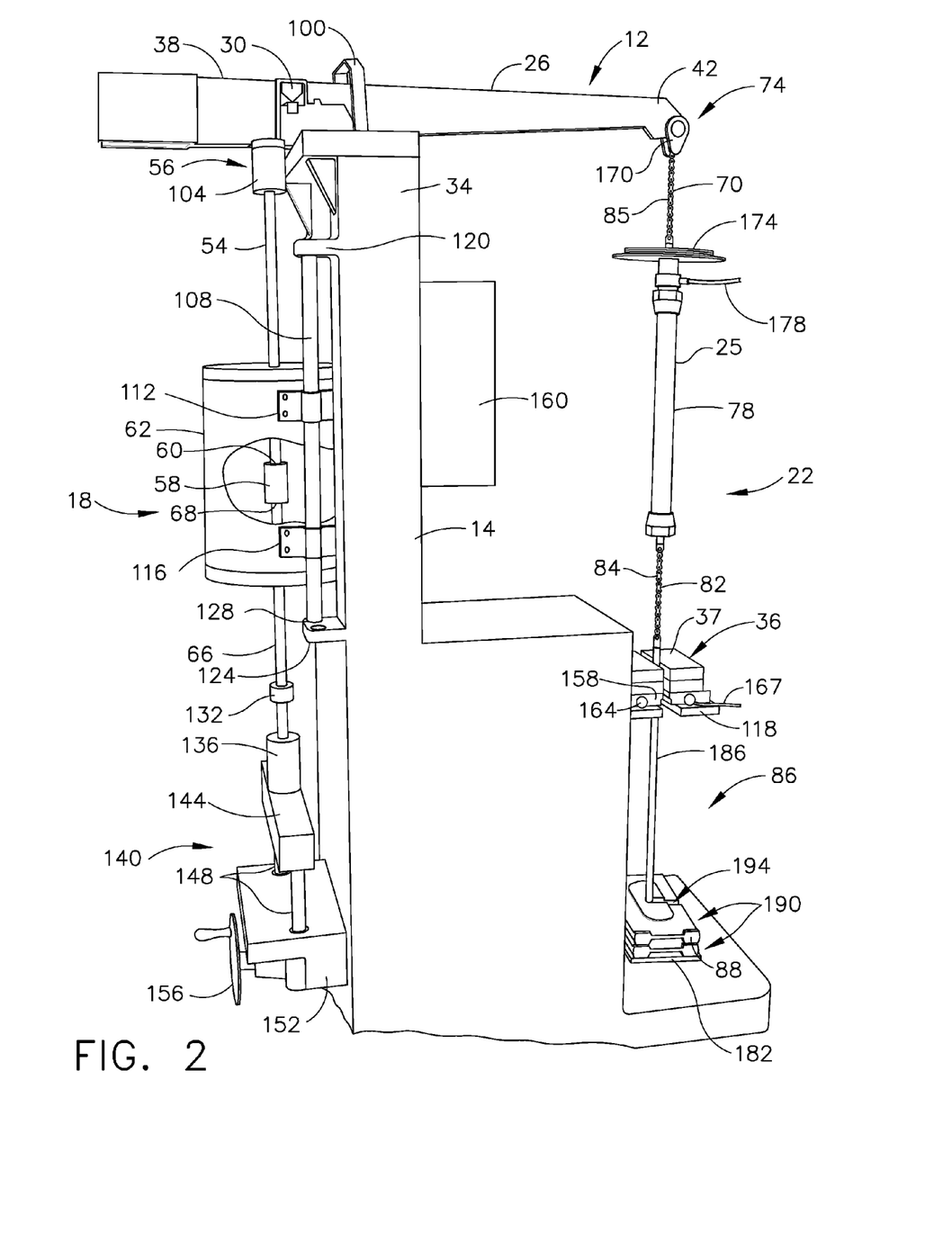
FIG. 2 is a detailed perspective view illustration of the apparatus illustrated in FIG. 1.

A more detailed embodiment of the tensile testing system 10, illustrated in FIG. 2, includes a generally U-shaped containment bracket 100 is attached to the top end 34 of frame 14 to keep arm 26 from pivoting or swinging too much either up or down about pivot point 30. The containment bracket 100 prevents the arm 26 from falling off of frame 14. An upper universal joint 104 is used at point to connect or attach the upper end of upper pull rod 54 to the load train end 38 of arm 26. A generally cylindrical mounting column 108 is attached to or mounted on furnace 62 by spaced apart upper and lower hinges 112, 116. The column 108 is pivotally mounted to the frame 14 by an upper bracket 120 having a circular recess (not shown) for receiving the upper end of column 108 and a lower bracket 124 also having a circular recess 128 for receiving the lower end of column 108.

An inline load cell 132 is mounted on lower pull rod 66 between the respective upper and lower ends thereof to directly measure the load being applied to test specimen 58. A lower universal joint 136 connects or attaches the lower end of lower pull rod 66 to a vertically movable cross-head assembly indicated generally as 140. Cross-head assembly 140 includes a generally horizontally extending cross-head 144 connected or attached to or otherwise associated with a generally vertically extending and spaced apart pair of rods 148 that are connected or attached to a horizontal base 152. A manual turn crank 156 is mounted on the base 152 for vertically moving or adjusting the position of the load train section 18 either upwardly or downwardly relative to frame 14. A furnace control box 160 is mounted on frame 14 and is connected to furnace 62 by control cables or lines (not shown) to control the environmental conditions (e.g., temperature, pressure, gas surrounding test specimen 58, etc.) within the furnace 62.

A pivoting connector 170 is used at the joint 74 to connect or attach the load adjusting end 42 of arm 26 to the upper connector 70. The upper connector 70 is illustrated herein as a flexible link or upper chain 85. The upper chain 85 is connected to an R-ratio or minimum load pan 174. Load pan 174 is connected or attached to the upper end of the fluidic mechanical muscle 78. The muscle 78 includes a fluid inlet and outlet line 178 for pressurizing and depressurizing muscle 78. The lower end of the muscle 78 is connected or attached to the lower connector 82, illustrated herein as a flexible link or lower chain 84.

Because the lower chain 84 is flexible, it provides sufficient slack when muscle 78 is in an extended state so that the first load 86 is completely or substantially completely reduced, i.e., there is no force or stress exerted by the first load 86 on test specimen 58. The lower chain 84 provides a mechanism for decoupling (e.g., mechanical decoupling) at least the principal portion of the load (i.e., first load 86) from test specimen 58 when the load is reduced during that portion of the testing cycle. The lower chain 84 is connected or attached to the first load 86 that includes a horizontal weight platform 182. An elongated weight receiving rod 186 is connected or attached to the weight platform 182 and extends generally vertically upwardly therefrom. The weight receiving rod 186 is then connected or attached to the lower chain 84. One or more weights 190 of similar or different mass can be loaded onto platform 182 and are configured with a slot 194 so that weights 190 can be securely received by rod 186.

Referring to FIGS. 1 and 2, a second cyclic loading system 96 includes a second controller 98 to cycle a second loading on the test specimen 58 by controlling a second load adjusting mechanism 35 used for applying and reducing a second load 36 attached to the lower connector 82 that is connected or attached, at its upper end, to the lower end of muscle 78. Whereas, the first cyclic loading system 92 was designed for sustained-peak low cycle fatigue (SPLCF) and hold time testing, to examine the fatigue crack growth behavior over time of materials used to make gas turbine engine components creep-rupture testing. The second cyclic loading system 96 is designed to perform over-peak or multiple loadings on the test specimen 58 on a creep-rupture testing frame and system.

Figure 3:
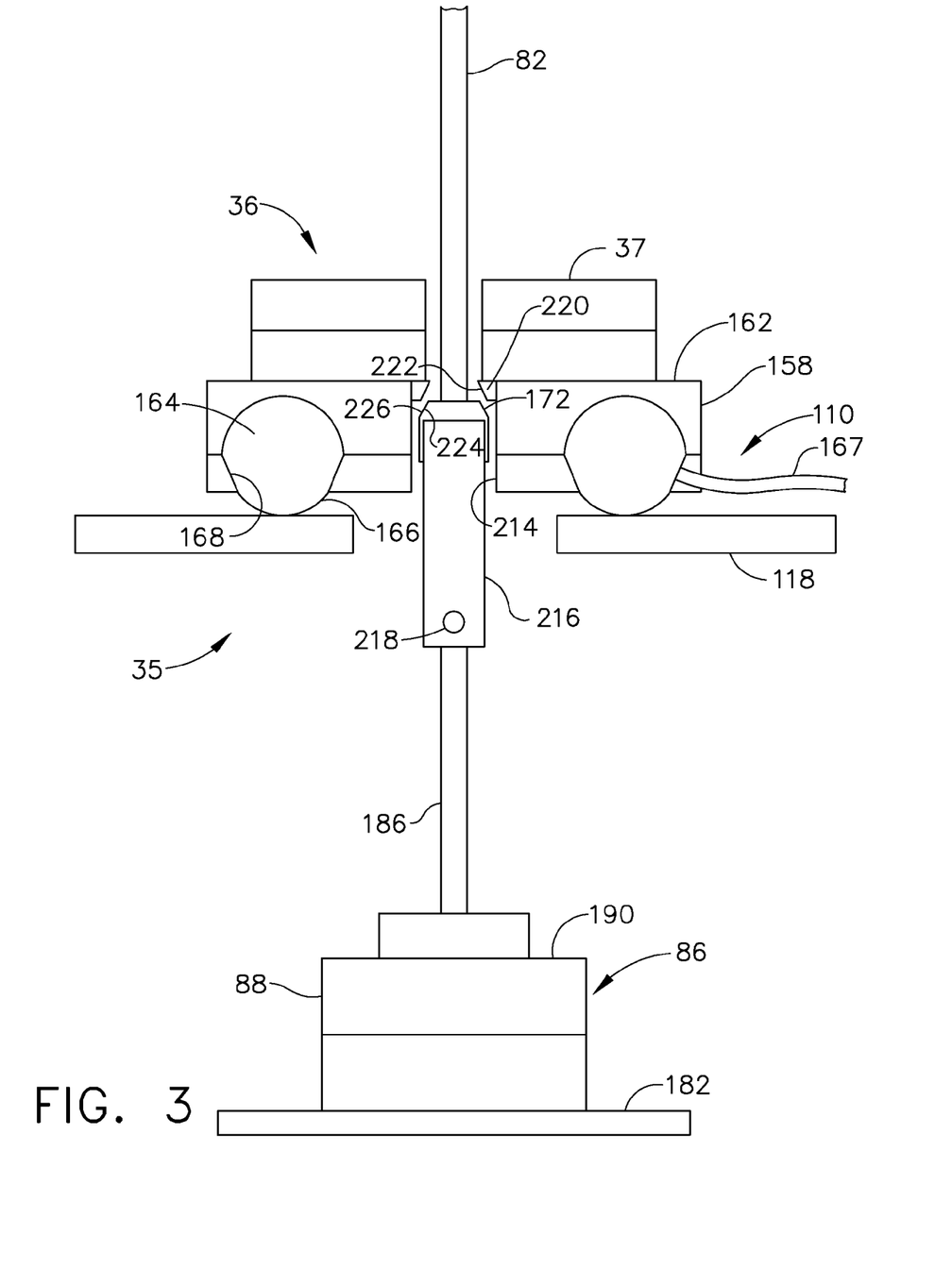
FIG. 3 is a cross sectional view illustration of a device for over-peak loading on the apparatus illustrated in FIG. 2.

Referring to FIGS. 2 and 3, the second load adjusting mechanism 35 is illustrated herein as an inflatable over-peak device 110 that rests or is supported on a support plate 118 mounted to the frame 14. The over-peak device 110 includes a hollow housing 158 with a flat top 162 for supporting the second load 36 illustrated as the second weights 37. An inflatable bladder 164 disposed within the housing 158 includes a bladder lower portion 166 which extends out of an opening 168 at a bottom of the housing 158 when the bladder 164 is inflated. Either the housing 158 or the bladder 164 when it is sufficiently inflated rests on the support plate 118. The bladder 164 is inflated or deflated with an air supply line 167.

The housing 158 includes a hollow hub 214 surrounding the lower connector 82. An adjustable collar clamp 216 includes a collar 172 and is adjustably clamped to a weight receiving rod 186 of the lower connector 82 with a vertical adjustment screw 218. The housing 158 includes an annular inner shoulder 220 with a downwardly facing chamfer 222 which engages an annular outer shoulder 224 with an upwardly facing chamfer 226 of the collar 172 when the bladder 164 is deflated. When the bladder 164 is deflated, the inner shoulder 220 rests on the outer shoulder 224 and the second load 36 produced by the second weights 37 is applied to the specimen 58 through the receiving rod 186 and the muscle 78. When the bladder 164 is inflated, the inner shoulder 220 raises up off of the outer shoulder 224 and the second weights 37 rest on the support plate 118 and the second load 36 no longer is applied to the specimen 58. Thus, the second load 36 may be cyclicly applied to the specimen 58 by deflating and inflating the bladder 164 cyclicly under the control of the second controller 98.

Figure 6:
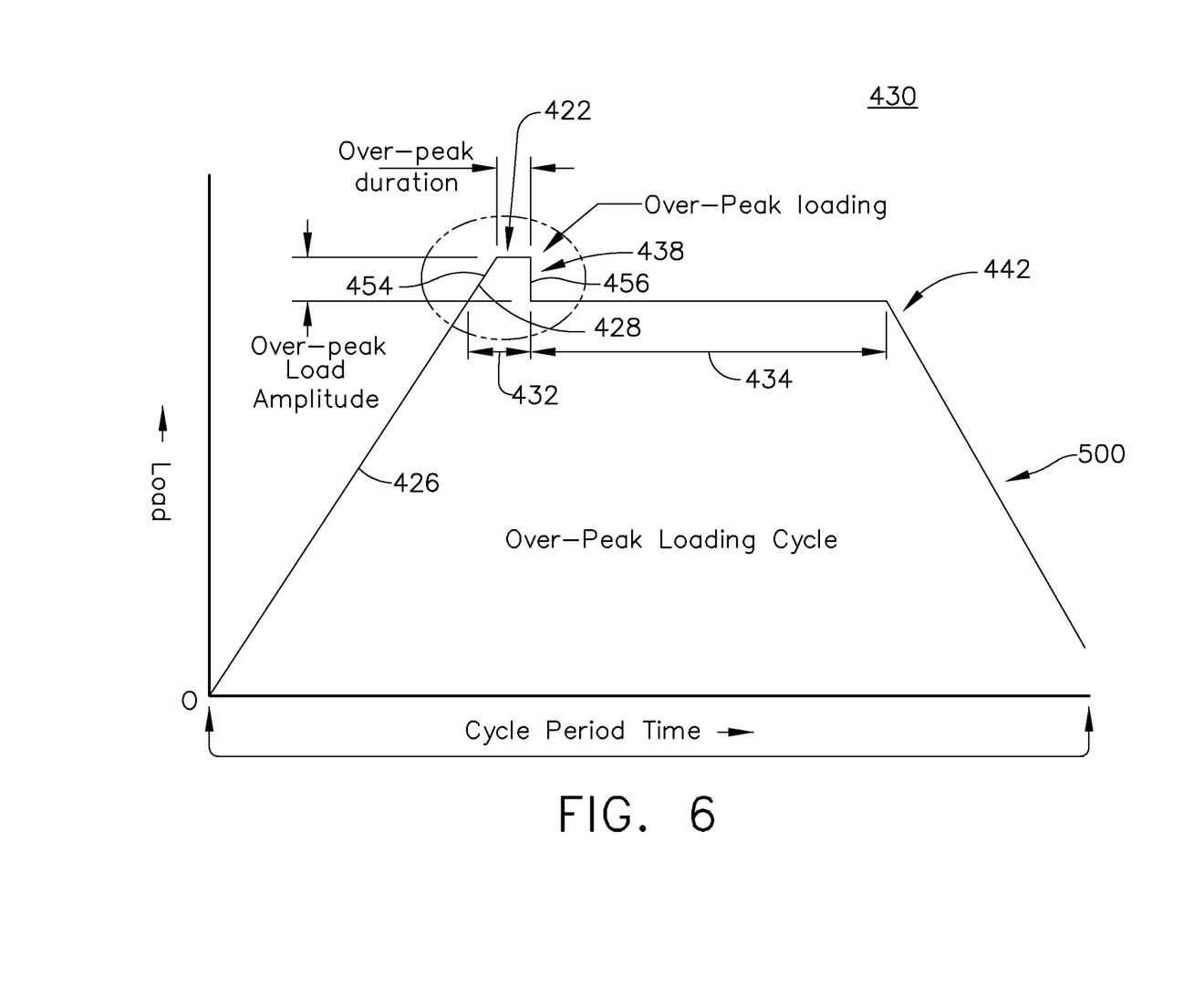
FIG. 6 is an enlarged view of a single cycle in the illustrative graphical plot illustrated in FIG. 5.

The second load 36 is additive with the first load 86. The first and second electronic controllers 94, 98 are operable to provide control of first and second loading rates 426, 428 and first and second dwell periods 432, 434 of first and second cycles 438, 442 respectively as illustrated in FIG. 6. The first cycle 438 is illustrated herein as an over-peak loading cycles and includes the first and second loads 86, 36. The second load 36 is applied by deflating the bladder 164. The second cycle 442 is illustrated herein as a hold time loading cycle and includes only the first load 86. The hold time loading cycle is created by inflating the bladder 164.

Figure 4:
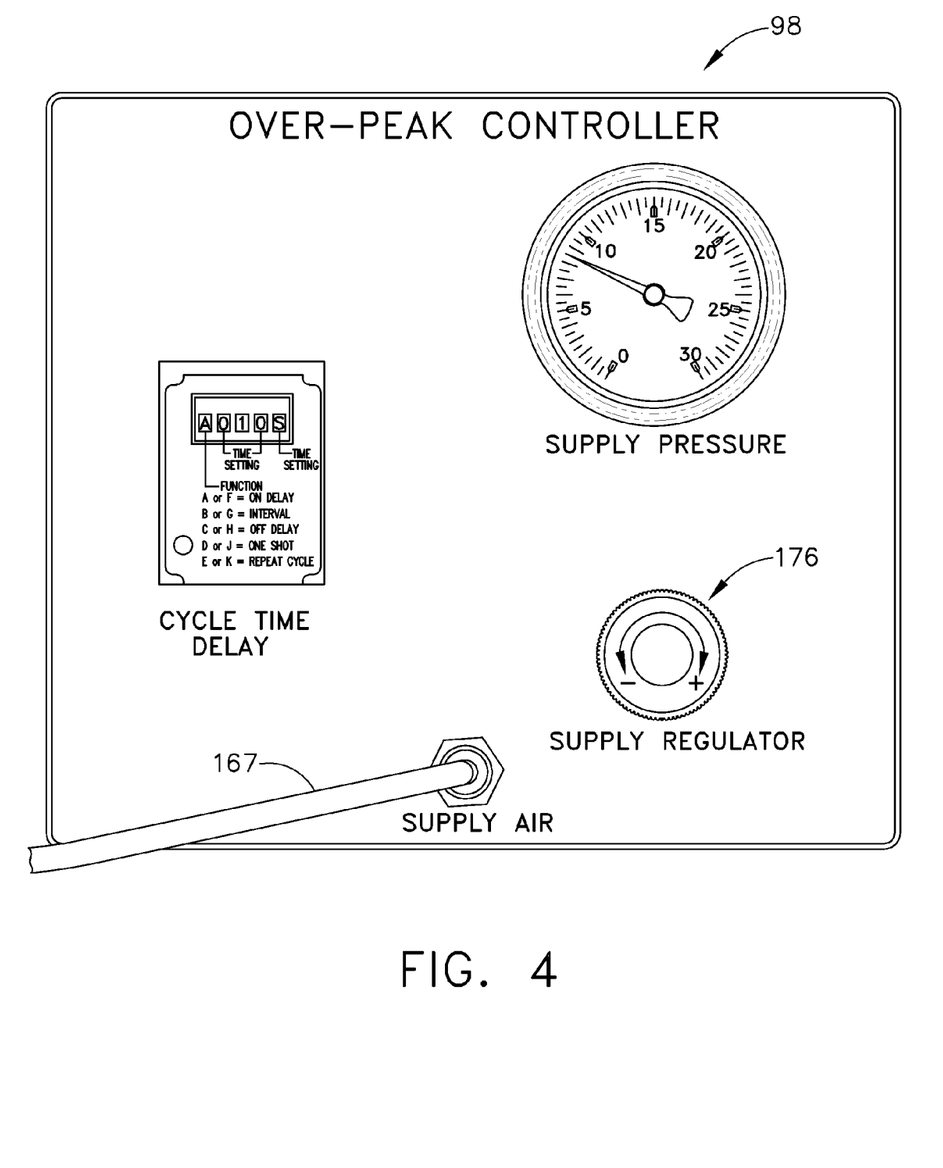
FIG. 4 is an elevational view illustration of a control panel for over-peak testing in the apparatus illustrated in FIG. 2.

The second electronic controller 98, illustrated in FIG. 4, provides load lifting capability via pressure control and the over-peak second dwell period 434 via a time delay relay. The second cyclic loading system 96 may be installed on existing lever-arm creep-rupture frames and allows multiple applied mechanical loading, such as an over-peak loading as described above. The second electronic controller 98 is illustrated as including an air supply regulator 176 for supplying the air used to inflate the bladder 164 through the air supply line 167 at a desired supply pressure.

Figure 5:
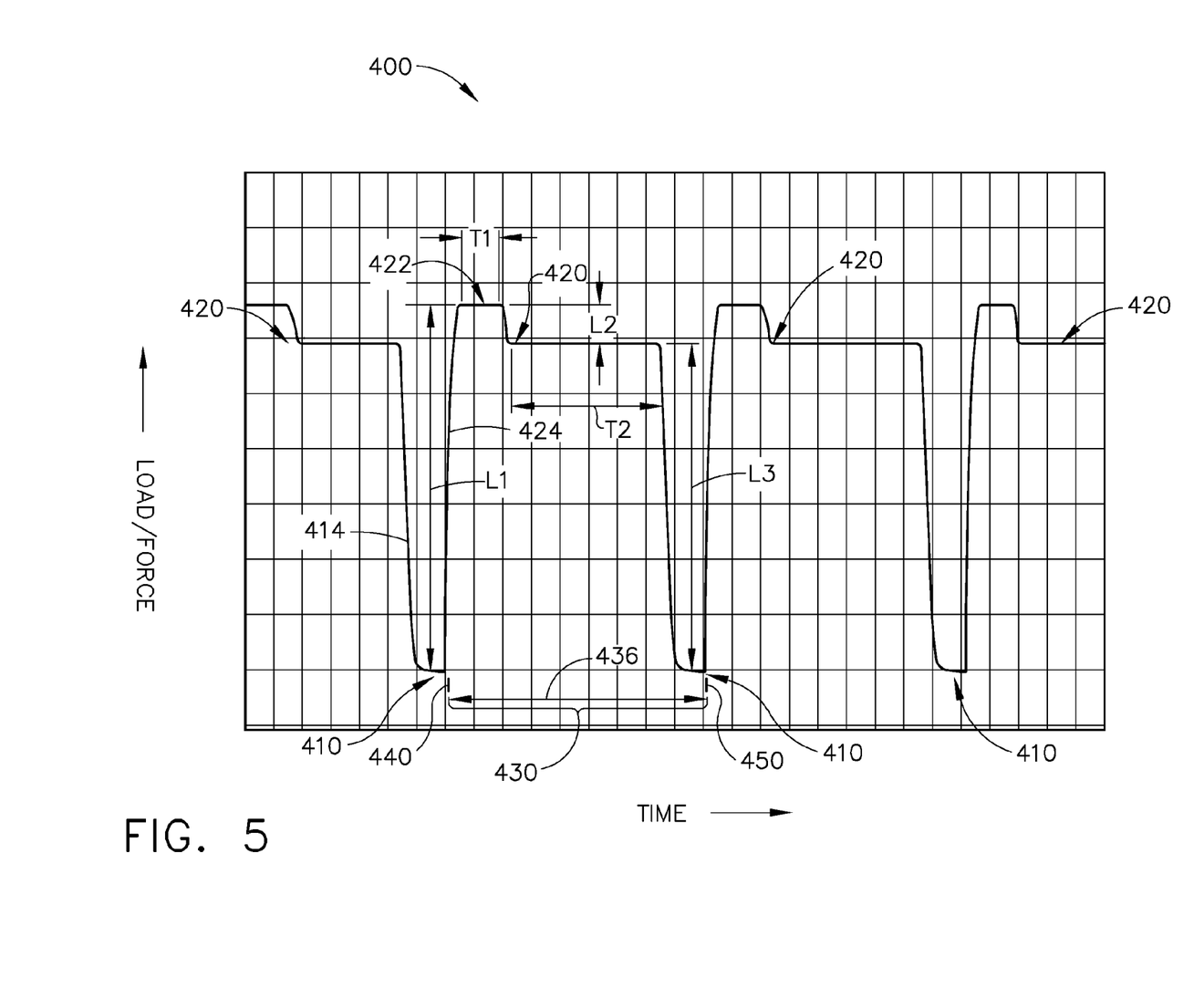
FIG. 5 is an illustrative graphical plot of a over-peak test that can be carried out using the apparatus illustrated in FIGS. 1-4.

FIG. 5 is an illustrative graphical plot 400 of a sustained-peak low cycle fatigue (SPLCF) test with over-peak loading that can be carried out using the system and apparatus of FIGS. 1-4. The graphical plot 400 of the SPLCF test has a series of valleys indicated as 410 which represent the reduction of the load on the test specimen along the portions of plot 400 indicated by a first downward slope 414 during the reducing (load decreasing) phase of the first cycle 438. The graphical plot 400 includes a series of first plateaus 420 which represent the sustained application (holding) of a combined load L1 which is the combination of the first and second weights 86, 36 produced by the first and second weights 88, 37 respectively on the test specimen 58. It is held for a first time period T1 which is controlled by the time delay setting on the over-peak controller or second controller 98 illustrated in FIG. 4.

Removal of the over-peak load L2 is performed by inflating the bladder 164. A second period T2 represents the hold time or peak loading of the first load 86, illustrated as the first weights 88, on the test specimen 58. L3 represents the reduction of load 86 by the deflation of muscle 78 in FIG. 3 while the bladder 164 is inflated.

The graphical plot 400 also includes a series of second plateaus 422 which represent the application (holding) of a hold time or peak load of the second cycle 442, represented by the second load 36 produced by the second weights 37, on the test specimen 58. The first upward slope 424 represents the loading (load increasing) phase of the first cycle 438. The application and reduction of the load in an SPLCF test is relatively rapid and the application of the peak and over-peak loads (see first and second plateaus 420, 422) in the SPLCF test is held or sustained at specified level for a given or discrete period of time.

Because of the repeated application and reduction of the load in the SPLCF test, graphical plot 400 represents a plurality of first and second cycles 438, 442 where the load is applied, held/sustained and then reduced. A combined cycle 430 (including both the first and second cycles 438 and 442) has a period 436, a start point 440, and an end point 450.

FIG. 6 is an enlarged graphical plot 500 of a single combined cycle 430 illustrated in FIG. 5. The over-peak loading has an over-peak amplitude equal to the second weights 37 and an over-peak duration controlled by the second controller 98. A second upward slope 454 represents the over-peak loading (load increasing) phase of the test cycle. A second downward slope 456 represents the over-peak load reducing (load decreasing) phase of the test cycle. The first and second cycles 438, 442 are illustrated herein as peak loading and over-peak loading cycles.

The present invention has been described in an illustrative manner. It is to be understood that the terminology which has been used is intended to be in the nature of words of description rather than of limitation. While there have been described herein, what are considered to be preferred and exemplary embodiments of the present invention, other modifications of the invention shall be apparent to those skilled in the art from the teachings herein and, it is, therefore, desired to be secured in the appended claims all such modifications as fall within the true spirit and scope of the invention.

Accordingly, what is desired to be secured by Letters Patent of the United States is the invention as defined and differentiated in the following claims.

What is claimed is:

1. A test specimen tensile testing apparatus comprising:
    a first load adjusting mechanism for cyclically applying and reducing a first load on the test specimen,
    a second load adjusting mechanism used for cyclically applying and reducing a second load,
    the first and second loads being tensile loads, and
    first and second controllers controllingly connected to the first and second load adjusting mechanisms and operable for independently cycling the first and second loads respectively on the test specimen.

2. A tensile testing apparatus as claimed in claim 1, further comprising the first and second controllers operable for cycling the first and second loads to be additive on the test specimen.

3. A tensile testing apparatus as claimed in claim 2, further comprising the first and second controllers operable for cycling the first and second loads for peak loading and over-peak loading the specimen respectively.

4. A tensile testing apparatus as claimed in claim 3, further comprising the first and second controllers operable for controlling first and second loading rates and first and second dwell periods of first and second cycles of loading on the test specimen respectively.

5. A tensile testing apparatus as claimed in claim 1, further comprising the second load adjusting mechanism including an inflatable over-peak device that rests or is supported on a support plate mounted to a frame of the tensile testing apparatus.

6. A tensile testing apparatus as claimed in claim 5, further comprising:
the inflatable over-peak device including a hollow housing with a flat top for supporting the second load,
an inflatable bladder disposed within the housing, and
a bladder lower portion which extends out of an opening at a bottom of the housing when the bladder is inflated.

7. A tensile testing apparatus as claimed in claim 6, further comprising the first and second controllers operable for cycling the first and second loads to be additive on the test specimen.

8. A tensile testing apparatus as claimed in claim 7, further comprising the first and second controllers operable for cycling the first and second loads for peak loading and over-peak loading the specimen respectively.

9. A tensile testing apparatus as claimed in claim 8, further comprising the first and second controllers operable for controlling first and second loading rates and first and second dwell periods of first and second cycles of loading on the test specimen respectively.

10. A test specimen tensile testing apparatus comprising:
a load train section connected to the test specimen,
a pivotable lever arm extending generally horizontally and pivotable on a frame of the tensile testing apparatus,
a first load adjusting mechanism for cyclically applying and reducing a first load on the test specimen,
a second load adjusting mechanism used for cyclically applying and reducing a second load,
the first and second loads being tensile loads,
the first and second load adjusting mechanisms extending generally vertically downwardly from a load adjusting end of the lever arm,
the load train section extending generally vertically downwardly from a load train end of the lever arm, and
first and second controllers controllingly connected to the first and second load adjusting mechanisms and operable for independently cycling the first and second loads respectively on the test specimen.

11. A tensile testing apparatus as claimed in claim 10, further comprising the first and second controllers operable for cycling the first and second loads to be additive on the test specimen.

12. A tensile testing apparatus as claimed in claim 11, further comprising the first and second controllers operable for cycling the first and second loads for peak loading and over-peak loading the specimen respectively.

13. A tensile testing apparatus as claimed in claim 12, further comprising the first and second controllers operable for controlling first and second loading rates and first and second dwell periods of first and second cycles of loading on the test specimen respectively.

14. A tensile testing apparatus as claimed in claim 10, further comprising the second load adjusting mechanism including an inflatable over-peak device that rests or is supported on a support plate mounted to a frame of the tensile testing apparatus.

15. A tensile testing apparatus as claimed in claim 14, further comprising:
the inflatable over-peak device including a hollow housing with a flat top for supporting the second load,
an inflatable bladder disposed within the housing, and
a bladder lower portion which extends out of an opening at a bottom of the housing when the bladder is inflated.

16. A tensile testing apparatus as claimed in claim 15, further comprising the first and second controllers operable for cycling the first and second loads to be additive on the test specimen.

17. A tensile testing apparatus as claimed in claim 16, further comprising the first and second controllers operable for cycling the first and second loads for peak loading and over-peak loading the specimen respectively.

18. A tensile testing apparatus as claimed in claim 17, further comprising the first and second controllers operable for controlling first and second loading rates and first and second dwell periods of first and second cycles of loading on the test specimen respectively.

19. A tensile testing apparatus as claimed in claim 10, further comprising the first load adjusting mechanism including a fluidic mechanical muscle that contracts and extends in length for cyclically applying and reducing the first load and the second load adjusting mechanism including an inflatable over-peak device that rests or is supported on a support plate mounted to a frame of the tensile testing apparatus.

20. A tensile testing apparatus as claimed in claim 19, further comprising:
the inflatable over-peak device including a hollow housing with a flat top for supporting the second load,
an inflatable bladder disposed within the housing, and
a bladder lower portion which extends out of an opening at a bottom of the housing when the bladder is inflated.

21. A tensile testing apparatus as claimed in claim 20, further comprising the first and second controllers operable for cycling the first and second loads to be additive on the test specimen.

22. A tensile testing apparatus as claimed in claim 21, further comprising the first and second controllers operable for cycling the first and second loads for peak loading and over-peak loading the specimen respectively.

23. A tensile testing apparatus as claimed in claim 22, further comprising the first and second controllers operable for controlling first and second loading rates and first and second dwell periods of first and second cycles of loading on the test specimen respectively.

24. A method for over-peak load testing a test specimen on a tensile testing apparatus, the method comprising:
mounting a test specimen in a load train section of a tensile testing apparatus having a pivotable lever arm extending generally horizontally and pivotable on a frame of the tensile testing apparatus,
the load train section extending generally vertically downwardly from a load train end of the lever arm,
cyclically applying and reducing tensile first and second loads with first and second load adjusting mechanisms respectively on the test specimen,
the first and second load adjusting mechanisms extending generally vertically downwardly from a load adjusting end opposite from the load train end of the lever arm, and
independently cycling the first and second loads using first and second controllers controllingly connected to the first and second load adjusting mechanisms respectively.

25. A method as claimed in claim 24, further comprising:
the first load adjusting mechanism including a fluidic mechanical muscle that contracts and extends in length and the cyclically applying and reducing the first load includes contracting and extending the fluidic mechanical muscle in length respectively, the second load adjusting mechanism including an inflatable over-peak device that rests or is supported on a support plate mounted to a frame of the tensile testing apparatus, the inflatable over-peak device including a hollow housing supporting the second load, an inflatable bladder disposed within the housing, a bladder lower portion which extends out of an opening at a bottom of the housing when the bladder is inflated, and the cyclically applying and reducing the second load includes deflating and inflating the bladder respectively.

26. A method as claimed in claim 25, further comprising applying the first and second loads together for over-peak loading of the specimen and removing the second load while holding the first load constant for peak loading.

27. A method as claimed in claim 26, further comprising controlling first and second loading rates and first and second dwell periods of first and second cycles during the cycling of the first and second loads respectively wherein the second cycle is substantially shorter than the first cycle.

28. A method as claimed in claim 27, further comprising the first and second loading rates being the same.

* * * * *